US012127920B2

(12) United States Patent
Piantoni et al.

(10) Patent No.: US 12,127,920 B2
(45) Date of Patent: Oct. 29, 2024

(54) METHOD FOR FORMING AND FOLDING ABSORBENT SANITARY ARTICLES

(71) Applicant: GDM S.p.A., Bologna (IT)

(72) Inventors: Matteo Piantoni, Bologna (IT); Alessandro Zavalloni, Bologna (IT)

(73) Assignee: GDM S.P.A., Bologna (IT)

( * ) Notice: Subject to any disclaimer, the term of this patent is extended or adjusted under 35 U.S.C. 154(b) by 59 days.

(21) Appl. No.: 18/069,068

(22) Filed: Dec. 20, 2022

(65) Prior Publication Data

US 2023/0201047 A1 Jun. 29, 2023

(30) Foreign Application Priority Data

Dec. 23, 2021 (IT) .......................... 102021000032477

(51) Int. Cl.
*A61F 13/00* (2024.01)
*A61F 13/15* (2006.01)

(52) U.S. Cl.
CPC .. *A61F 13/15747* (2013.01); *A61F 13/15731* (2013.01)

(58) Field of Classification Search
CPC ..................... A61B 13/15747; A61B 13/49011
See application file for complete search history.

(56) References Cited

U.S. PATENT DOCUMENTS

| 8,556,790 | B2 | 10/2013 | Fujita |
| 2002/0138063 | A1 | 9/2002 | Kuen et al. |
| 2007/0044608 | A1 | 3/2007 | Franke |
| 2013/0255861 | A1* | 10/2013 | Schneider ......... A61F 13/15593 156/161 |
| 2014/0080692 | A1* | 3/2014 | Lenser ................... B65H 45/22 156/60 |
| 2015/0083309 | A1* | 3/2015 | Long ...................... B29C 65/10 156/161 |
| 2015/0173957 | A1* | 6/2015 | Schneider ......... A61F 13/15723 493/374 |
| 2016/0175161 | A1* | 6/2016 | Zink, II ............ A61F 13/15747 493/345 |
| 2016/0175166 | A1* | 6/2016 | Zink, II ............ A61F 13/51496 156/227 |

(Continued)

OTHER PUBLICATIONS

Italian Search Report dated Jun. 19, 2022 from counterpart Italian Patent Application No. 102021000032477.

*Primary Examiner* — Eyamindae C Jallow
(74) *Attorney, Agent, or Firm* — SHUTTLEWORTH & INGERSOLL, P.L.C.; Timothy J. Klima

(57) ABSTRACT

A method for forming and folding an absorbent sanitary article includes the steps of preparing a continuous, multilayer web and feeding it in a feed direction, applying a succession of absorbent pads, spaced from each other, on the continuous, multilayer web, folding the absorbent pads on the continuous multilayer web, temporarily fastening the folded absorbent pads to the continuous, multilayer web, making a succession of lines of weakness in the continuous, multilayer web between consecutive absorbent articles, folding a first flap of each absorbent article towards the corresponding absorbent pad, folding a second flap of each absorbent article towards the corresponding absorbent pad; folding the first flap or the second flap includes tearing the continuous, multilayer web at the lines of weakness, thereby separating the absorbent articles.

10 Claims, 3 Drawing Sheets

(56) References Cited

U.S. PATENT DOCUMENTS

2016/0175167 A1* 6/2016 Sauer ................ A61F 13/15731
  156/204
2016/0331600 A1* 11/2016 Polidori .............. A61F 13/4902
2017/0056254 A1* 3/2017 Lenser .............. A61F 13/15764
2017/0304124 A1* 10/2017 Lenser .............. A61F 13/15747

* cited by examiner

METHOD FOR FORMING AND FOLDING ABSORBENT SANITARY ARTICLES

This application claims priority to Italian Patent Application 102021000032477 filed Dec. 23, 2021, the entirety of which is incorporated by reference herein.

BACKGROUND OF THE INVENTION

This invention relates to a method for forming and folding absorbent sanitary articles. More specifically, this invention relates to a method for separating individual diapers of the kind known as "refastenable" or "T-shaped" diapers from a continuous web and folding them.

The most common state-of-the-art diapers for children and adults are substantially of two kinds: refastenable diapers and "pant style" diapers.

Refastenable diapers are essentially in the shape of an H, where the legs of the H are the parts of the diaper that are wrapped around the wearer's waist, while the connecting portion of the H is the crotch provided with an absorbent pad. Generally speaking, at the end portions of the legs of the H, these diapers comprise tabs which, when the diaper is being worn, are used for fastening it around the wearer's waist.

Pant style diapers, on the other hand, look and are worn like pants, with elastic waistbands which are welded or joined by a permanent connection.

In recent times, another type of diaper, also known as "refastenable diaper" is becoming more common and this type of diaper, when open, is basically in the shape of a T. In this type of diaper, the elastic waistband is the horizontal portion of the T and the crotch, comprising the absorbent pad, corresponds to the stem portion of the T. The crotch portion is folded towards the waistband, both in use and during manufacturing, while the end portions of the waist are in turn folded towards the center line and fixed to the folded crotch portion.

A special feature of this type of diaper is that it can be worn like pants, by inserting the legs into the corresponding openings but, when necessary, it can be adjusted at the waist like a traditional diaper.

In effect, the end portions of the waist are fixed to the outside of the crotch portion by releasable fastening means.

During manufacture, refastenable diapers are cut from a continuous web and folded; basically, the absorbent pads are attached, at regular intervals, to a continuous elastic band which is then cut after the pads have been folded onto it.

An example of a system and a method for folding such diapers is described in document U.S. Pat. No. 8,556,790B2, where the individual diapers are separated from each other by a step of cutting which is carried out on a folding wheel.

In practice, the folding wheel, besides the movable parts needed for folding the products, also comprises a plurality of anvils and a cutting device which must be synchronized with the wheel in such a way as to cut the continuous web before the diapers are folded.

The folding wheel is mechanically highly complex and heavy.

In this sector, therefore, there is a need for a method for forming and folding refastenable diapers that is simpler than the methods known in the prior art.

SUMMARY OF THE INVENTION

More specifically, this invention has for an aim to provide a method for forming and folding refastenable diapers which easily and effectively allows cutting the continuous web into individual products and folding the individual products.

This aim is achieved by a method for forming and folding absorbent sanitary articles comprising the technical features described in one or more of the accompanying claims. The dependent claims correspond to possible different embodiments of the invention.

According to a first aspect, this invention relates to a method for forming and folding an absorbent sanitary article.

The absorbent sanitary article comprises a waistband, an absorbent pad which extends from an intermediate portion of the waistband and which separates a first and a second flap of the waistband. The absorbent sanitary article comprises a first closing element at one end of the first flap and a second closing element at one end of the second flap.

The absorbent pad, at least in use or during manufacture of the absorbent sanitary article, is folded towards the waistband to define a crotch of the absorbent sanitary article and the first and second flaps are folded onto the folded absorbent pad and fixed thereto by the first closing element and the second closing element, respectively, to define a pant-like article.

The forming and folding method comprises the following steps:
preparing a continuous, multilayer web and feeding it in a feed direction;
applying a succession of absorbent pads, spaced from each other, on the continuous, multilayer web, preferably so they jut outward therefrom;
folding the absorbent pads onto the continuous, multilayer web;
temporarily fastening the folded absorbent pads to the continuous, multilayer web;
applying a succession of the first closing elements on the continuous, multilayer web;
applying a succession of the second closing elements on the continuous, multilayer web.

Each absorbent pad is interposed between one of the first closing elements and one of the second closing elements.

The forming and folding method comprises the following steps:
making a succession of lines of weakness in the continuous, multilayer web between each second closing element and the first closing element following it in the feed direction of the continuous multilayer web; each line of weakness is disposed between consecutive absorbent articles in the feed direction of the continuous multilayer web.

The method comprises the steps of:
folding the first flap of each absorbent article towards the corresponding absorbent pad;
folding the second flap of each absorbent article towards the corresponding absorbent pad.

The step of folding the first flap of each absorbent article towards the corresponding absorbent pad or the step of folding the second flap of each absorbent article towards the corresponding absorbent pad comprises tearing the continuous, multilayer web at the lines of weakness, thereby separating the absorbent articles.

Separating the distinct absorbent articles by pre-cutting and tearing makes it possible to do without sharp cutting devices. In the preferred case where folding and separating the absorbent articles are carried out on a folding wheel, the folding wheel is lighter, less complex and more compact than in prior art solutions since it does not need to be provided with web cutting devices.

According to an aspect, the step of folding the first flap of each absorbent article towards the corresponding absorbent pad is carried out before the step of folding the second flap of each absorbent article towards the corresponding absorbent pad.

According to an aspect, the step of folding the first flap of each absorbent article towards the corresponding absorbent pad is carried out after the step of folding the second flap of each absorbent article towards the corresponding absorbent pad.

According to an aspect, the step of folding the first flap of each absorbent article towards the corresponding absorbent pad is carried out at the same time as the step of folding the second flap of each absorbent article towards the corresponding absorbent pad.

According to an aspect, the step of folding the first flap of each absorbent article towards the corresponding absorbent pad comprises a step of attaching the first flap to the corresponding absorbent pad with the first closing element.

According to an aspect, the step of folding the second flap of each absorbent article towards the corresponding absorbent pad comprises a step of attaching the second flap to the corresponding absorbent pad with the second closing element.

According to an aspect, the step of temporarily fastening the folded absorbent pads to the continuous, multilayer web comprises a step of plastically deforming at least one portion of each folded absorbent pad and one portion of the continuous, multilayer web at the portion of the folded absorbent pads to create mechanical interference between the absorbent pads and the continuous, multilayer web.

According to an aspect, at least the steps of:
folding the first flap of each absorbent article towards the corresponding absorbent pad and:
folding the second flap of each absorbent article towards the corresponding absorbent pad,
are carried out on a folding wheel.

According to an aspect, the method comprises a step of retaining at least the continuous, multilayer web on the folding wheel.

BRIEF DESCRIPTION OF THE DRAWINGS

Further features and advantages of the invention are more apparent in the exemplary, hence non-limiting description which follows of a preferred but non-exclusive embodiment of a method for forming and folding absorbent sanitary articles.

The description is set out below with reference to the accompanying drawings which are provided solely for purposes of illustration without restricting the scope of the invention and in which.

DESCRIPTION OF THE PREFERRED EMBODIMENTS

Figure 8:
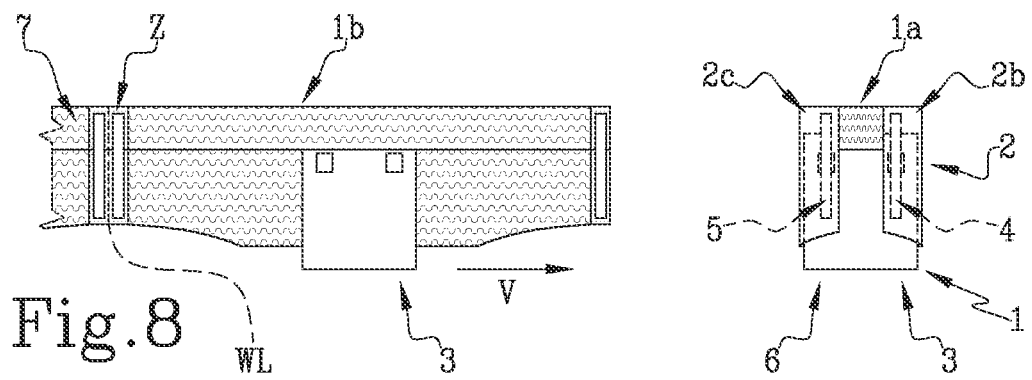

With reference to FIG. 8, the numeral 1 denotes a wearable absorbent sanitary article of the type known as "refastenable", hereinafter also referred to simply as "diaper".

The diaper 1 essentially comprises an elastic waistband or strip 2 and an absorbent pad 3 attached to the waistband 2.

The waistband 2 is, for example, a piece of a multilayer web comprising a first and a second web of non-woven fabric joined to each other. The elasticity of the waistband 2 is normally provided by elastics placed between the webs of non-woven fabric.

The absorbent pad 3 is attached to an intermediate portion 2a of the elastic waistband 2 from which it projects, when the diaper 1 is open, to form a T-shaped structure.

The elastic waistband 2 is the horizontal portion of the T and the absorbent pad 3 is the leg of the T.

In the elastic waistband 2, the absorbent pad 3 separates two portions, or wings, or side flaps 2b, 2c.

The article 1 comprises a first closing element 4 attached, at one end of the flap 2b, to the face of the flap 2b which, in use, is directed towards a wearer (not illustrated).

The article 1 comprises a second closing element 5 attached, at one end of the flap 2c, to the face of the flap 2c which, in use, is directed towards a wearer (not illustrated).

The closing elements 4 and 5 are of substantially known type and, in the example illustrated, extend along the corresponding edge of the respective flap.

When the article 1 is being used or during its manufacture, the absorbent pad 3 is folded towards the waistband 2 to define a crotch 6 of the article 1.

At least in these cases, the flaps 2b, 2c are folded onto the folded absorbent pad 3 and fastened to the same by the first closing element 4 and the second closing element 5, respectively.

In embodiments not illustrated, the article 1 may comprise a closing element attached to the absorbent pad 3 on the side opposite that of the wearer so that the closing elements 4, 5 of the elastic waistband 2 engage the closing element on the absorbent pad 3.

As illustrated schematically in FIG. 8, the diaper 1 in the closed configuration is substantially pant-like.

The forming and folding method comprises a step of preparing a continuous, multilayer web W intended to form a plurality of waistbands 2 and feeding it in a feed direction V along a feed path.

The web W comprises, for example, a first and a second web of non-woven fabric, joined to each other, and a plurality of elastics 7 interposed between them. At least part of these elastics is illustrated and labelled in the accompanying drawings. The elastics 7 are preferably spread across the full width of the web W.

The first and the second web may, for example, be glued and/or welded to each other, for example by ultrasounds, in substantially known manner.

Figure 1:
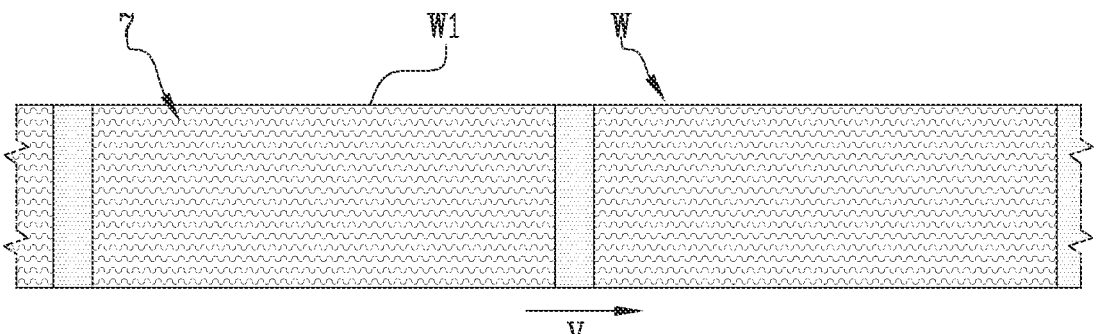
FIGS. 1 to 8 schematically illustrate a sequence of steps of a forming and folding method according to this disclosure.
Figure 2:
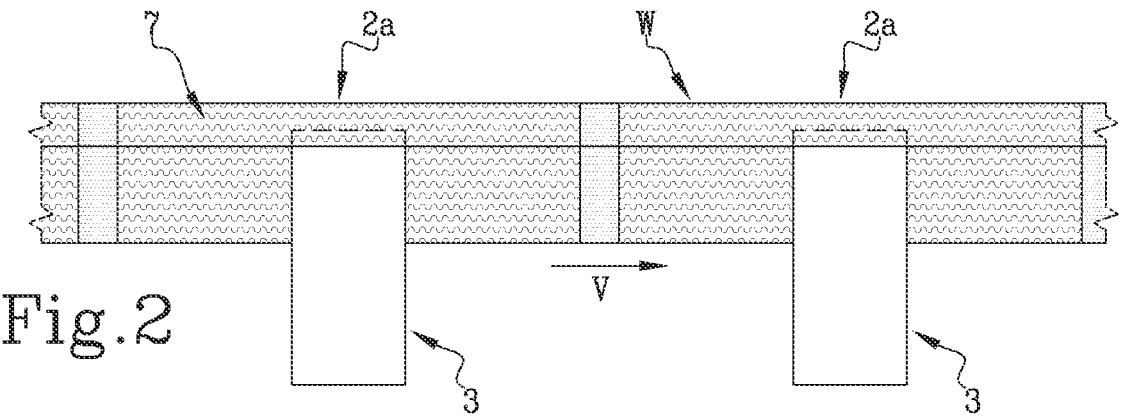

With reference to FIG. 2, the forming and folding method comprises a step of applying to the continuous multilayer web W—for example with glue and preferably so they jut outwards (that is, so they are in relief)—a succession of absorbent pads 3 spaced apart by a spacing which is at least a function of the size of the absorbent article 1.

Preferably, the method comprises a step of folding an edge W1 of the web W—the upper edge, looking at the drawings—onto the absorbent pads 3.

Next, the absorbent pads 3 are folded onto the web W about a folding line L which, in the example illustrated, is parallel to the web W and to the feed direction of the web W.

The method comprises a step of folding the absorbent pads 3 onto the continuous multilayer web W and a step of temporarily fastening the folded absorbent pads 3 to the continuous, multilayer web W.

Figure 3:
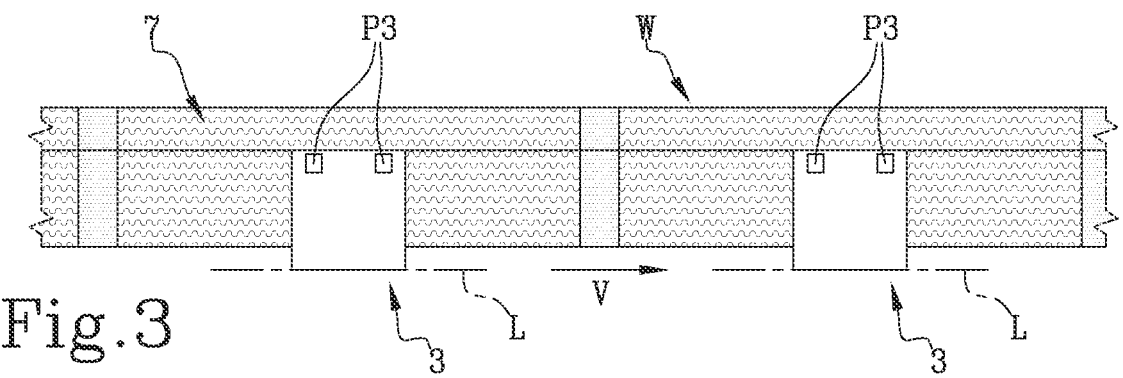

The absorbent pads 3 are fastened to the web W temporarily in such a way as to remain in a folded configuration, as illustrated in FIG. 3, until the remaining steps of the method are carried out on it.

Preferably, the step of temporarily fastening the folded absorbent pads 3 to the continuous, multilayer web W comprises a step of plastically deforming a portion P3 of the folded absorbent pads 3 and a portion PW of the continuous, multilayer web W located substantially at the portion P3 to create mechanical interference between the absorbent pads 3 and the continuous, multilayer web W.

Preferably, the step of plastically deforming is carried out by cold blanking and/or by thermomechanical blanking.

The method comprises a step of applying a succession of the first closing elements 4 and a succession of the second closing elements 5 on the continuous, multilayer web W.

Figure 4:
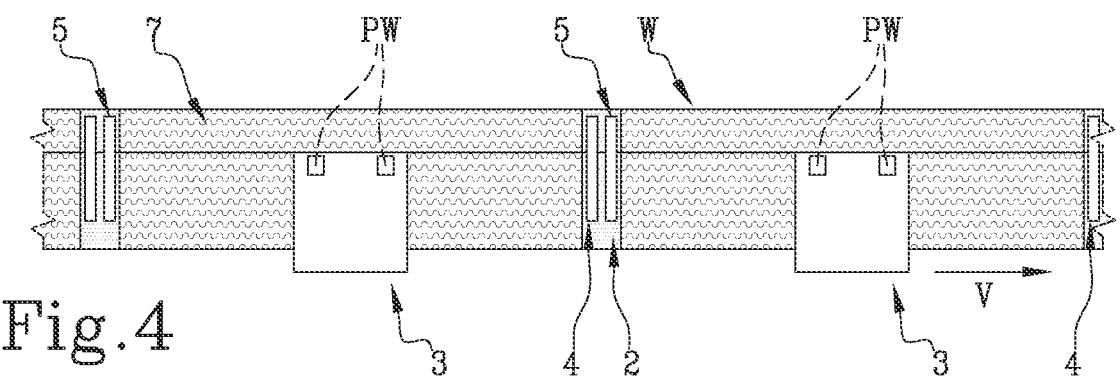

As illustrated by way of an example in FIG. 4, each absorbent pad 3 is interposed between a first closing element 4 and a second closing element 5.

In the case where the web W is formed of a first web glued to a second web with the elastics 7 interposed between them, the method may comprise a step of cutting or interrupting the elastics 7 in the zones where the closing elements 4, 5 are applied.

For example, the accompanying drawings illustrate zones Z at the closing elements 4, 5, where the elastics 7 have been cut or omitted.

In the case where the web W is formed of a first web glued tom a second web with the elastics 7 interposed between them, the method may comprise a step of cutting or interrupting the elastics 7 in the zones where the absorbent pads, 3 are applied.

In the case where the web W is formed of a first web welded to a second web with the elastics 7 interposed between them, the method may comprise a step of welding the first web to the second web except at the zones where the closing elements 4, 5 are applied.

In the case where the web W is formed of a first web welded to a second web with the elastics 7 interposed between them, the method may comprise a step of welding the first web to the second web except at the zones where the absorbent pads 3 are applied.

In the embodiment illustrated by way of example, the method comprises a step of contouring the web W between the absorbent pads 3.

Figure 5:
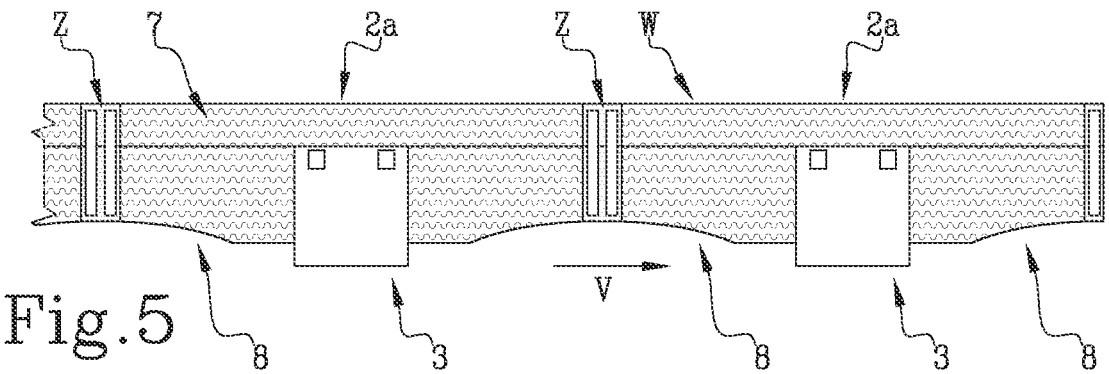
Figure 6:
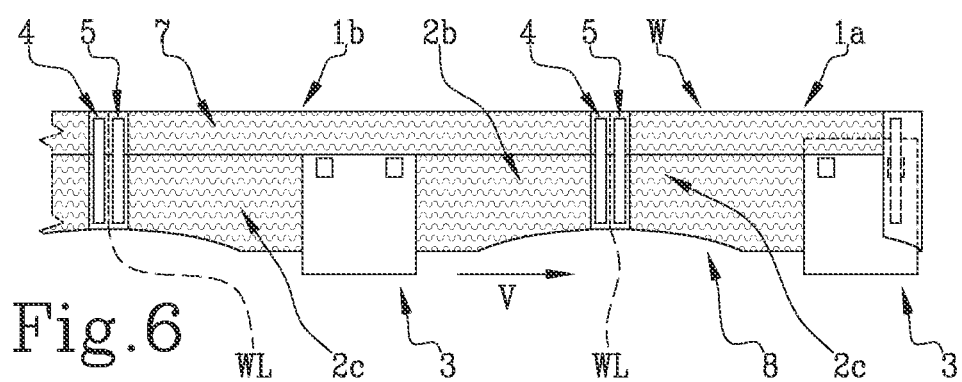

With reference to FIG. 5, it is noted, for example, that the web W comprises contours 8, where portions of the web W have been removed.

The method comprises a step of making a succession of lines of weakness WL in the continuous, multilayer web between each closing element 5 and the closing element 4 following it in the feed direction V, each line of weakness WL comprising, for example, a series of cuts which perforate the web W.

In practice, each line of weakness WL defines an end of the flap 2c of a first absorbent article 1a and the end of the flap 2b of a second absorbent article 1b following the first absorbent article 1a in the feed direction V.

Each line of weakness WL separates an absorbent article 1 from the one following it along the web W.

The forming and folding method comprises a step of folding the first flap 2b of each absorbent article 1 towards the corresponding absorbent pad 3 and a step of folding the second flap 2c of each absorbent article 1 towards the corresponding absorbent pad 3.

Folding the first flap 2b of each absorbent article 1 towards the corresponding absorbent pad 3 or folding the second flap 2c of each absorbent article 1 towards the corresponding absorbent pad 3 comprises tearing the continuous, multilayer web W at the lines of weakness WL, thereby separating the absorbent articles 1 from each other.

Figure 7:
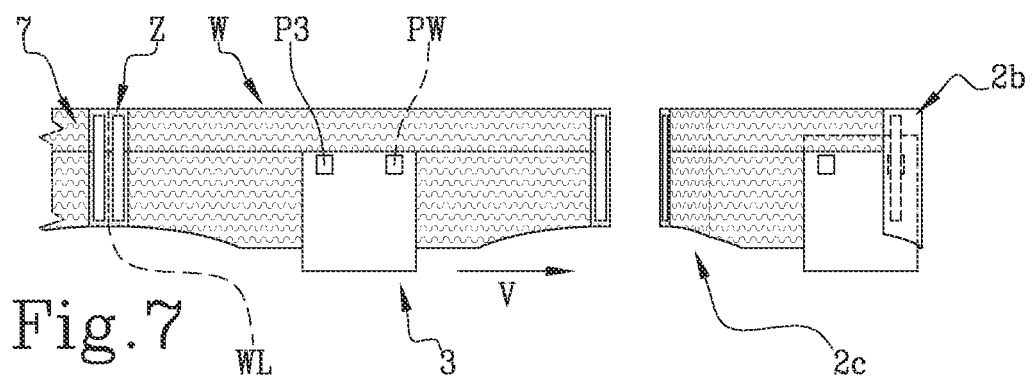

In the example illustrated, with reference in particular to FIG. 7, it is by folding the second flap 2c that the absorbent web W is torn at the lines of weakness WL.

In the embodiment of the method schematically represented in the accompanying drawings, the step of folding the first flap 2b of the absorbent article 1 towards the corresponding absorbent pad 3 is carried out before the step of folding the second flap 2c of the absorbent article 1 towards the corresponding absorbent pad 3.

In an embodiment of the method not illustrated, the step of folding the first flap 2b of the absorbent article 1 towards the corresponding absorbent pad 3 is carried out after the step of folding the second flap 2c of the absorbent article 1 towards the corresponding absorbent pad 3.

In an embodiment of the method not illustrated, the step of folding the first flap 2b of the absorbent article 1 towards the corresponding absorbent pad 3 is carried out at the same time as the step of folding the second flap 2c of the absorbent article 1 towards the corresponding absorbent pad 3.

According to this method, the step of folding the first flap 2b of the absorbent article 1 towards the corresponding absorbent pad 3 comprises a step of attaching the first flap 2b to the corresponding absorbent pad 3 with the first closing element 4.

According to this method, the step of folding the second flap 2c of the absorbent article 1 towards the corresponding absorbent pad 3 comprises a step of attaching the second flap 2c to the corresponding absorbent pad 3 with the second closing element 5.

Figure 9:
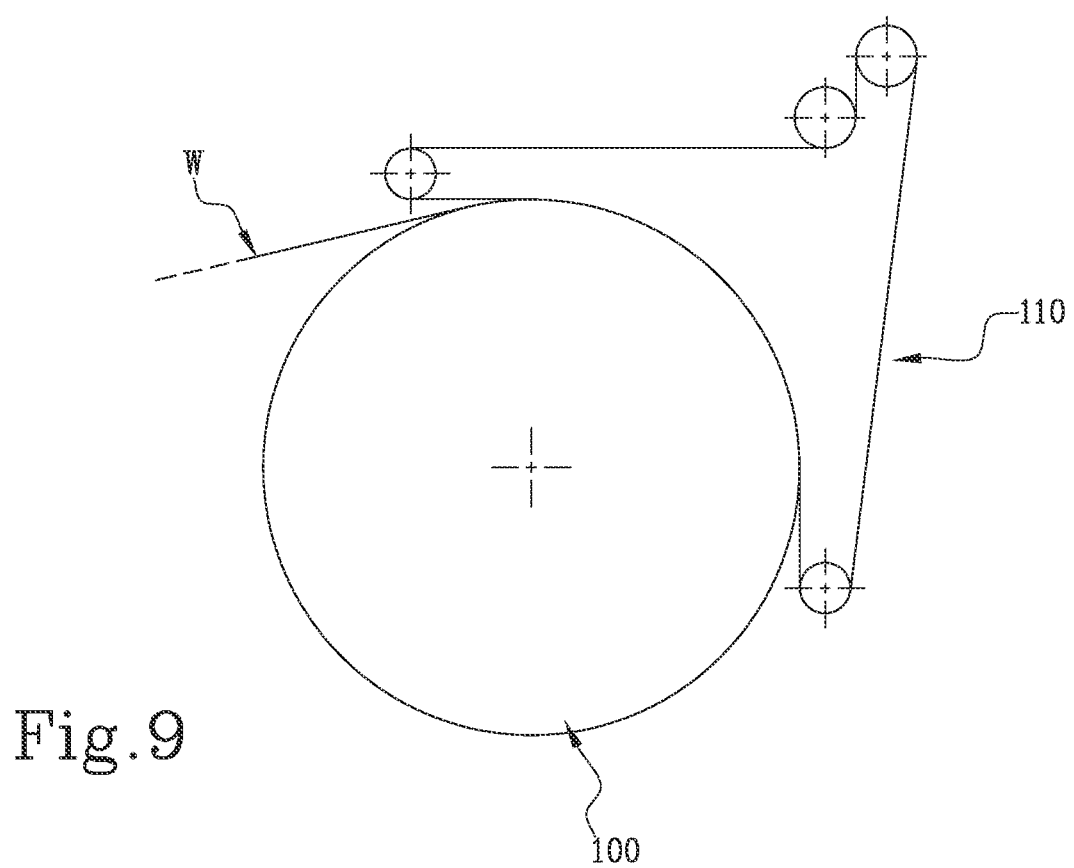
FIG. 9 shows a highly schematic representation of a folding wheel for implementing a forming and folding method according to this disclosure.

With reference to the schematic representation of FIG. 9, it is noted that the step of folding the first flap 2b of each absorbent article 1 towards the corresponding absorbent pad 3 and the step of folding the second flap 2c of each absorbent article 1 towards the corresponding absorbent pad 3 are carried out on a folding wheel 100.

The folding wheel 100 is, for example, of the type illustrated in document U.S. Pat. No. 8,556,790, except for the anvils 31 and the cutting devices 30.

The method, at least when it is implemented on a folding wheel 100, comprises a step of retaining at least the continuous, multilayer web W on the folding wheel 100, for example, via suction systems or belt systems, an example of which is labelled 110.

The solution as described herein brings important advantages. In particular, separating the distinct absorbent articles by pre-cutting and tearing makes it possible to do without sharp cutting devices. In the preferred case where folding and separating the absorbent articles are carried out on a folding wheel, the folding wheel is lighter, less complex and more compact than in prior art solutions since it does not need to be provided with web cutting devices.

The invention claimed is:

1. A method for forming and folding an absorbent sanitary article comprising a waistband, an absorbent pad extending from an intermediate portion of the waistband, the absorbent pad separating a first flap and a second flap of the waistband, the absorbent sanitary article comprising a first closing element at one end of the first flap and a second closing element at one end of the second flap, the absorbent pad being, at least in use, folded towards the waistband to define a crotch of the absorbent sanitary article, and the first and second flaps being folded onto the folded absorbent pad and fixed thereto by the first closing element and the second closing element, respectively, to define pants, the forming and folding method comprising:
- preparing a continuous, multilayer web and feeding the continuous, multilayer web in a feed direction;
- applying a succession of absorbent pads, spaced from each other, on the continuous, multilayer web;
- folding the absorbent pads onto the continuous, multilayer web;
- temporarily fastening the folded absorbent pads to the continuous, multilayer web;
- applying a succession of the first closing elements on the continuous, multilayer web;
- applying a succession of the second closing elements on the continuous, multilayer web, each absorbent pad being interposed between one of the first closing elements and one of the second closing elements;
- making a succession of lines of weakness in the continuous, multilayer web between each second closing element and the first closing element following the each second closing element in the feed direction, each line of weakness being made and disposed between consecutive absorbent sanitary articles in the feed direction;
- folding the first flap of each absorbent sanitary article towards the corresponding absorbent pad;
- folding the second flap of each absorbent sanitary article towards the corresponding absorbent pad,
- the step of folding the first flap of each absorbent sanitary article towards the corresponding absorbent pad or the step of folding the second flap of each absorbent sanitary article towards the corresponding absorbent pad comprising a step of tearing the continuous, multilayer web at the lines of weakness, thereby separating the absorbent sanitary articles.

2. The forming and folding method according to claim 1, wherein the step of folding the first flap of the absorbent sanitary article towards the corresponding absorbent pad is carried out before the step of folding the second flap of the absorbent sanitary article towards the corresponding absorbent pad.

3. The forming and folding method according to claim 1, wherein the step of folding the first flap of the absorbent sanitary article towards the corresponding absorbent pad is carried out after the step of folding the second flap of the absorbent sanitary article towards the corresponding absorbent pad.

4. The forming and folding method according to claim 1, wherein the step of folding the first flap of the absorbent sanitary article towards the corresponding absorbent pad is carried out at a same time as the step of folding the second flap of the absorbent sanitary article towards the corresponding absorbent pad.

5. The forming and folding method according to claim 1, wherein the step of folding the first flap of the absorbent sanitary article towards the corresponding absorbent pad comprises attaching the first flap to the corresponding absorbent pad with the first closing element.

6. The forming and folding method according to claim 1, wherein the step of folding the second flap of the absorbent sanitary article towards the corresponding absorbent pad comprises attaching the second flap to the corresponding absorbent pad with the second closing element.

7. The forming and folding method according to claim 1, wherein the temporarily fastening the folded absorbent pads to the continuous, multilayer web comprises plastically deforming at least one portion of each folded absorbent pad and one portion of the continuous, multilayer web at the at least one portion of each folded absorbent pad to create mechanical interference between the absorbent pads and the continuous, multilayer web.

8. The forming and folding method according to claim 7, wherein the step of plastically deforming is carried out by cold blanking or by thermomechanical blanking.

9. The forming and folding method according to claim 1, wherein at least the steps of:
- folding the first flap of each absorbent sanitary article towards the corresponding absorbent pad and:
- folding the second flap of each absorbent sanitary article towards the corresponding absorbent pad, are carried out on a folding wheel.

10. The forming and folding method according to claim 9, and further comprising a step of retaining at least the continuous, multilayer web on the folding wheel.

* * * * *